(12) United States Patent
Maser et al.

(10) Patent No.: US 12,390,267 B2
(45) Date of Patent: Aug. 19, 2025

(54) BIPOLAR SEALING INSTRUMENT WITH PARTLY AUTOMATED ACTUATING MECHANISM

(71) Applicant: Aesculap AG, Tuttlingen (DE)

(72) Inventors: Thomas Maser, Zimmern ob Rottweil (DE); Eugen Herner, Villingen-Schwenningen (DE); Erik Walberg, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 674 days.

(21) Appl. No.: 17/293,937

(22) PCT Filed: Nov. 15, 2019

(86) PCT No.: PCT/EP2019/081482
§ 371 (c)(1),
(2) Date: May 14, 2021

(87) PCT Pub. No.: WO2020/099633
PCT Pub. Date: May 22, 2020

(65) Prior Publication Data
US 2022/0008119 A1    Jan. 13, 2022

(30) Foreign Application Priority Data
Nov. 16, 2018  (DE) ............... 10 2018 128 870.0

(51) Int. Cl.
*A61B 18/14*  (2006.01)
*A61B 17/00*  (2006.01)
(Continued)

(52) U.S. Cl.
CPC .............. *A61B 18/1445* (2013.01); *A61B 2017/00398* (2013.01); *A61B 2017/2845* (2013.01);
(Continued)

(58) Field of Classification Search
CPC ............ A61B 18/1445; A61B 18/1206; A61B 18/1482; A61B 18/1442;
(Continued)

(56) References Cited

U.S. PATENT DOCUMENTS 9,517,068 B2  12/2016  Shelton, IV et al.
9,820,823 B2  11/2017  Richmond et al.
(Continued)

FOREIGN PATENT DOCUMENTS

CN    103889360 A    6/2014
EP      3135225 A2    3/2017
(Continued)

OTHER PUBLICATIONS

Office Action received in Chinese Application No. 201980074075.5 dated Nov. 8, 2023, with translation, 12 pages.
(Continued)

*Primary Examiner* — Khadijeh A Vahdat
*Assistant Examiner* — Marina Delaney Templeton
(74) *Attorney, Agent, or Firm* — Christopher A. Rothe; CM Law

(57) ABSTRACT

A bipolar sealing instrument includes a first actuating mechanism for manual actuation of a tool provided at a distal instrument tip at least in a low-load working force range. A second actuating mechanism includes an electric motor configured to be automatically activated when a high-load working force range is reached, in order to subsequently transfer the tool into a high-load working posture/position in a motor-assisted or fully automatic manner supporting the manual actuation.

19 Claims, 7 Drawing Sheets

(51) Int. Cl.
*A61B 17/28* (2006.01)
*A61B 18/00* (2006.01)
*A61B 18/12* (2006.01)

(52) U.S. Cl.
CPC ............... *A61B 2018/00589* (2013.01); *A61B 2018/0063* (2013.01); *A61B 2018/00958* (2013.01); *A61B 2018/126* (2013.01)

(58) Field of Classification Search
CPC .. A61B 2017/00398; A61B 2017/2845; A61B 2017/00017; A61B 2017/00734; A61B 2017/2927; A61B 2017/00477; A61B 2017/00473; A61B 2017/320095; A61B 2017/320092; A61B 2017/320094; A61B 2017/2837; A61B 2017/2903; A61B 2017/2912; A61B 2017/2913; A61B 2017/2915; A61B 2017/2916; A61B 2017/2923; A61B 2017/2925; A61B 2018/00589; A61B 2018/0063; A61B 2018/00958; A61B 2018/126; A61B 2018/00208; A61B 2090/064; A61B 2090/0811; A61B 34/70; A61B 34/37; A61B 17/2833; A61B 17/2841; A61B 17/2909
See application file for complete search history.

(56) References Cited

U.S. PATENT DOCUMENTS

| | | | |
|---|---|---|---|
| 10,034,719 B2 | 7/2018 | Richmond et al. | |
| 2003/0025723 A1* | 2/2003 | Olien | G09B 23/285 715/701 |
| 2007/0191828 A1 | 8/2007 | Houser et al. | |
| 2008/0077131 A1 | 3/2008 | Yates et al. | |
| 2008/0223904 A1 | 9/2008 | Marczyk | |
| 2013/0103050 A1 | 4/2013 | Richmond et al. | |
| 2015/0209059 A1* | 7/2015 | Trees | A61B 18/1445 606/205 |
| 2015/0209573 A1 | 7/2015 | Hibner et al. | |
| 2016/0089175 A1* | 3/2016 | Hibner | A61B 17/282 606/205 |

FOREIGN PATENT DOCUMENTS

| | | |
|---|---|---|
| JP | 2007229454 A | 9/2007 |
| JP | 2008073531 A | 4/2008 |
| JP | 2008220956 A | 9/2008 |
| KR | 1020070079048 A | 8/2007 |
| RU | 136968 U1 | 1/2014 |
| SU | 1223894 A1 | 4/1986 |
| SU | 1253631 A1 | 8/1986 |
| WO | 2013059643 A1 | 4/2013 |

OTHER PUBLICATIONS

Office Action received in Russian Application No. 2021117196/14 dated Jan. 24, 2022, with translation, 11 pages.
Search Report received in Russian Application No. 2021117196/14 dated Jan. 24, 2022, with translation, 4 pages.
Office Action received in Japanese Application No. 2021-526367 dated Sep. 11, 2023, with translation, 16 pages.
Written Opinion received in International Application No. PCT/EP2019/081482 dated Feb. 25, 2020, with translation, 13 pages.
International Search Report received in Application No. PCT/EP2019/081482 dated Feb. 25, 2020, with translation, 5 pages.
Search Report received in German Application No. 10 2018 128 870.0 dated Aug. 23, 2019, with translation, 18 pages.
1 Office Action received in Chinese Application No. 201980074075.5 dated May 10, 2024, with translation, 12 pages.
Office Action received in Chinese Application No. 201980074075.5 dated Nov. 18, 2024, with translation, 10 pages.
Office Action received in Korean Application No. 10-2021-7018360 dated Sep. 19, 2024, with translation, 12 pages.
Examination Report received in European Application No. 19 809 003.7 dated Dec. 19, 2024, with translation, 13 pages.
Office Action received in Chinese Application No. 201980074075.5 dated Mar. 13, 2025, with translation, 14 pages.

* cited by examiner

BIPOLAR SEALING INSTRUMENT WITH PARTLY AUTOMATED ACTUATING MECHANISM

CROSS-REFERENCE TO RELATED APPLICATIONS

This application is the United States national phase entry of International Application No. PCT/EP2019/081482, filed Nov. 15, 2019, and claims the benefit of priority of German Application No. 10 2018 128 870.0, filed Nov. 16, 2018. The contents of International Application No. PCT/EP2019/081482 and German Application No. 10 2018 128 870.0 are incorporated by reference herein in their entireties.

FIELD

The present disclosure relates to a surgical instrument, preferably a bipolar sealing instrument, having a tool effector provided at a distal instrument tip.

BACKGROUND

Bipolar sealing instruments are mainly used in minimally invasive surgery. They are used both to prepare (patient) tissue, i.e., for example, to pluck, spread or push the tissue out of the way, and to clamp the tissue in order to seal it in a single work step by heating and, if necessary, also cut it. For this purpose, the tool formed on the instrument tip has branches or jaw parts that can be moved relative to each other and are suitable for gripping tissue. Electrodes are arranged on the branches for cauterizing and, if necessary, also for cutting through/cutting the tissue, for example by applying direct current or high-frequency alternating current. Alternatively or additionally, an additional tool, such as a blade, may be provided for mechanically severing the tissue.

Known surgical bipolar sealing instruments generally have forceps-like tissue clamping effectors, which are actuated purely mechanically. When handling the sealing instrument during tissue preparation, only small actuation forces are required, but a high degree of sensitivity as well as a great deal of skill on the part of the user. On the other hand, for cauterizing/sealing and possibly cutting the patient tissue, high actuation forces are necessary to apply a required effector-jaw clamping force. To make this possible, a large actuation stroke of a (single) actuation lever or handle element must be provided in order to be able to generate larger clamping forces on the effector with the appropriate reduction. Accordingly, tissue preparation takes place with the handle element relatively wide open, making it more difficult to use for users with small hands. Furthermore, the portion of the actuation stroke available for tissue preparation is limited, making sensitive actuation of the instrument more difficult. On the other hand, in the working position in which the tissue is cauterized and possibly cut, the handle element is strongly compressed, so that a user can only hold this working position with a strong curvature of the hand and thus the use of the sealing and cutting instrument leads to increased physical strain, especially for users with large hands.

Known mechanically operated sealing and cutting instruments consequently always make a compromise between an ergonomic design of the instrument, better operability when clamping the tissue, and fine motor operability when preparing the tissue. In order to optimize this, known solution approaches provide for complex operating mechanisms, in particular due to the multifunctional design (sensitive preparation and strong clamping), which may require a high level of user understanding and thus lead to a high potential for operating errors. For example, the instrument may be overloaded during clamping and thus destroyed, or the tissue may be clamped too weakly and thus incompletely sealed, leading to excessive damage and bleeding of the patient's tissue. Further exemplary possibilities of incorrect operation, which may be caused in particular by fatigue or cramping of the user, are too short and thus insufficient tissue sealing or imprecise, shaky guidance/handling of the instrument during preparation and/or clamping.

SUMMARY

Thus, it is an object of the present invention to provide a preferably bipolar sealing instrument of the TFT type, which avoids or at least mitigates the disadvantages described above. In particular, it is an object of the present invention to provide a bipolar sealing instrument, which is ergonomically designed, easy to operate and avoids operating errors.

The basic idea of the present invention for solving the foregoing problem is that the functions necessary for operating the instrument are distinguished based on the working force required, and associated working force ranges are defined. Subsequently, a separate actuating mechanism is provided for each of the various functions, and these actuating mechanisms are coupled in such a way that switching over or switching on of the same is performed automatically.

More specifically, the problem is solved by a bipolar sealing instrument, in particular a combined sealing and cutting instrument, having a first actuating mechanism for manually actuating a tool provided at a distal instrument tip at least in a low-load working force range. Further, the instrument has a second actuating mechanism comprising a motor, preferably an electric motor, which is configured to be automatically activated upon actuation of the sealing instrument according to the invention in a high-load working force range to subsequently transfer the tool to a high-load working posture/position in a motor-assisted or fully automatic manner supporting or replacing the manual actuation.

In other words, the tool is manually actuated in a low-load working force range, allowing sensitive tissue preparation of patient tissue. In a high-load working force range, in which tissue clamping or build-up of the clamping force necessary for sealing the patient tissue takes place, the (electric) motor is automatically switched on and the tool is motor-actuated by the motor or actuation of the tool is at least motor-assisted.

The low-load working force range is a range in which the low forces necessary for preparing the patient tissue are required, and the high-load working force range is a range in which tissue clamping of the patient tissue takes place under high force. The high-load working posture/position is a position of the tool and actuating mechanisms in which the clamping force required to seal the patient tissue is achieved.

By operating the tool purely manually in the low-load working force range, the patient tissue can be prepared with little force, i.e., with virtually no fatigue, and the user receives direct, tactile feedback regarding the applied forces, allowing for highly precise operation. Furthermore, since the clamping force no longer has to be built up purely manually, the actuation stroke provided for this purpose (clamping stroke) can be significantly reduced. Consequently, the total actuation stroke (of a single handle element), which includes both the clamping stroke and an actuation stroke provided for tissue preparation (preparation stroke), is also reduced.

(That is, the clamping stroke and the preparation stroke are actuated/provided by a common or single handle element). Thus, a larger actuation stroke is available as the preparation stroke, thereby enabling easier, precise actuation of the tool. In addition, the start and end positions of the handle element can be ergonomically optimized for manual tissue preparation.

In addition, switching on the electric motor in the high-load working force range allows high actuation or clamping forces to be built up without thereby impairing instrument guidance, which is why this can also be carried out in a calm and controlled manner during tissue clamping. This prevents unnecessary tissue damage. Furthermore, user fatigue is largely prevented and operation of the instrument is unproblematic even for physically weaker users. Motorized assistance or fully automated tissue clamping can ensure that the minimum tissue clamping/compression required for method-appropriate vessel sealing is performed. Furthermore, the division of the actuating mechanism into first and second actuating mechanisms allows for ease of design.

The working force ranges, in particular the achievement of the high-load working force range and/or the high-load working posture/position, can be determined directly or indirectly by sensors, for example by pressure, position or strain sensors. I.e. the corresponding working forces/actuating forces do not have to be measured directly, but can also be detected indirectly, e.g. derived from known mechanical variables such as a spring force as well as a position or displacement detection. For this purpose, for example, strain gauges, incremental encoders for displacement measurement, contacts or contact distances or switches can be used. If necessary, a rotary encoder or torque sensor can be provided to monitor the operation of the electric motor.

The electric motor may be a linear or a rotary motor. In the case of a rotary motor, a gearbox may further be provided for translating or reducing the torque and speed and/or for converting the rotary motion into a linear motion, e.g., a screw gearbox with a threaded spindle and a spindle nut.

The tool/effector provided at the instrument tip preferably has branches that can be moved towards each other in a forceps-like manner, which can be used for gripping the tissue, as well as electrodes for sealing and, if necessary, for separating/cutting the patient tissue. In order to cut the tissue, an additional blade can also be provided in principle.

Preferably, the (handle element-free) second actuating mechanism is mechanically coupled to a handle element of the first actuating mechanism during an actuation in the high-load working force range, preferably via a guide pin mated with a guide groove. As a result, the engagement of the second actuating mechanism can be solved in a constructively simple manner. (In particular, the second actuating mechanism is not coupled to a separate handle element. The automatic engagement of the second actuating mechanism is effected by an actuation of the handle element of the first actuating mechanism). For example, an actuating lever, slider or knob can be provided as a handle element. Furthermore, it has proven useful if the second actuating mechanism is coupled to the tool, for example via the first actuating mechanism, by a spring element. This can serve as an emergency overload protection in case the electric motor is not actuated in a purely force-controlled manner but, for example, in a path-controlled manner and the tool encounters an unexpected resistance. When coupled via the first actuating mechanism, the spring element can additionally serve as an overload protection in case a user continues to actuate the handle element despite reaching the high-load working posture/position. Alternatively, the second actuating mechanism may be completely decoupled from the first actuating mechanism at least during actuation of the first actuating mechanism so that no force is transmitted to the second actuating mechanism during this time. In this case, the first actuating mechanism may optionally provide information about an actuation path or a position of the first actuating mechanism.

According to an advantageous embodiment, the second actuating mechanism is configured such that it can be reset from the high-load working posture/position fully automatically or with motorized assistance. The motorized assistance or reset enables a precisely controllable or adjustable reset from the high-load working posture/position, in particular during an unlatching process described later and associated with a further advantageous embodiment.

Preferably, a detection device is configured to sense a first threshold actuation force indicative of reaching the high-load working posture/position. Alternatively or additionally, reaching the high-load working posture/position may be detected by detecting a position (e.g., of the pull rod and/or the actuating lever) and/or an angle (e.g., of the actuating lever). Herein, when the first threshold actuation force is reached, at least one of the first and second actuating mechanisms latches and the electric motor is automatically deactivated, or the electric motor serves as a latching means.

In this way, it can be detected when the necessary clamping force for sealing the tissue has been reached, and thus it can be avoided that the tissue is not clamped sufficiently. It also ensures that no excessive load is applied to the tool or the actuating mechanisms, thus avoiding damage to the instrument. If the electric motor serves as the latching means, the high-load working posture/position is maintained by the electric motor. If at least one of the actuating mechanisms latches, the high-load working posture/position is maintained by the latching means (for example, on the instrument housing by a spring or spring-loaded latching element) and can be released by an initial manual force. In this case, the reset can be either completely manual and, if necessary, spring-assisted. It is possible to prevent activation of the electrodes for tissue sealing and, if necessary, tissue cutting, as long as the high-load working posture/position is not reached.

According to a first aspect of the present invention, the detection device may be configured to sense a second threshold actuation force indicative of reaching the high-load working force range. In this case, the electric motor of the second actuating mechanism is automatically activated when the second threshold actuation force is reached. That is, when the user applies a force to the handle element that reaches or exceeds the second threshold actuation force, the electric motor is automatically engaged. Since this actuation on the part of the user is also part of the workflow in common, in particular bipolar sealing instruments of the TFT type (thermal fusion technology), the correct operation of the instrument according to the invention is instinctive for the user and no or little additional training is required.

Advantageously, according to this aspect of the invention, the first and/or second actuating mechanism is configured to latch in the high-load working posture/position. Thus, the high-load working posture/position can be held securely and in a manner that conserves energy, and the latching can only be released by the user. In other words, the duration of the tissue clamping (clamping duration) and, if necessary, of the subsequent cutting process is determined by the user, so that the user can, for example, adjust a duration of the tissue clamping and sealing in particular depending on the tissue thickness and/or type.

Alternatively, the invention may be modified in that at least the second actuating mechanism is configured to be held in the high-load working posture/position by the electric motor. In this way, the reset of at least the second actuating mechanism by the electric motor can be fully automatic or motor-assisted, and thus can be safely controlled. Advantageously, no additional latching means need to be provided on the actuating mechanism and/or on the instrument housing, thus further simplifying the design and saving installation space, weight and costs.

In addition, the first and/or second actuating mechanism can advantageously be motor-releasable from the high-load working posture/position in a process-dependent manner, in particular after a predetermined time, or the motorized assistance can be initiated by a manual initial actuation, e.g. a tapping of the actuating lever. Alternatively, the first and/or second actuating mechanism may be manually releasable from the high-load working posture/position. A process-dependent release makes it possible to avoid errors by the user and to perform the tissue clamping based on specific values. Thereby, if necessary, the certain values can be adjustable depending on the type of an operation to be performed, i.e. on the type of tissue to be treated, and/or in a process-dependent manner. On the other hand, a manual release makes it possible to take into account experience of the user as well as, for example, current endoscopic images and to make individual adjustments accordingly.

According to a second, advantageous aspect of the invention, the first and/or second actuating mechanism latches when the high-load working force range is reached, and preferably the latching can be released by a motorized assistance triggered by a manual initial actuation. In this way, the user receives tactile and/or audible feedback when the high-load working force range is reached. Furthermore, if necessary, this can prevent further actuation of the instrument by the user in the high-load working force range, so that incorrect operation on the part of the user can be ruled out during tissue clamping and, if necessary, cutting. The motorized support can further ensure a smooth release of the latching, i.e. unlatching. Manual release by the user would be accompanied by jerking of the instrument.

Further, also according to the second aspect of the invention, it is convenient to configure the second actuating mechanism such that it is held in the high-load working posture/position by the electric motor. Similarly, according to this aspect, the second actuating mechanism, in particular the activation, an actuation duration and the deactivation of the electric motor, can be controlled in a process-dependent manner, in particular in dependence on a sealing and possibly cutting process. As already explained above, in this way user-side operating errors can be excluded and the duration of the tissue clamping and sealing can be set sufficiently but not excessively large. Preferably, the electric motor of the second actuating mechanism is automatically activated to achieve clamping of patient tissue when the first and/or second actuating mechanism is engaged and a sealing process is initialized. That is, only when both the placement of the tool by the user is completed (the latching is established) and the electrodes are activated by the user, the electric motor of the second actuating mechanism is switched on. It is particularly advantageous that the start of the clamping or the activation of the electric motor of the second actuating mechanism can also be started in a process-dependent manner, so that the clamping of the patient's tissue does not take an excessively long time and the patient's tissue is thus protected.

In particular, it is advantageous if a simple, tissue clamping-free coagulation/sealing can be performed when a sealing process is initialized while the first and/or second actuating mechanism is unlatched. In this way, the instrument can have both a sealing and possibly cutting function and an additional function of simple hemostasis.

BRIEF DESCRIPTION OF THE DRAWING FIGURES

Exemplary embodiments of a combined sealing and cutting instrument are described below, which is an example of a sealing instrument according to the disclosure, in this particular case a bipolar sealing instrument. In this context, the same elements are designated by the same reference characters. The embodiments are merely illustrative of the present invention and are not intended to limit the scope of protection defined by the claims. It is understood that different embodiments may be combined, elements may be interchanged or omitted.

DETAILED DESCRIPTION

Figure 1:
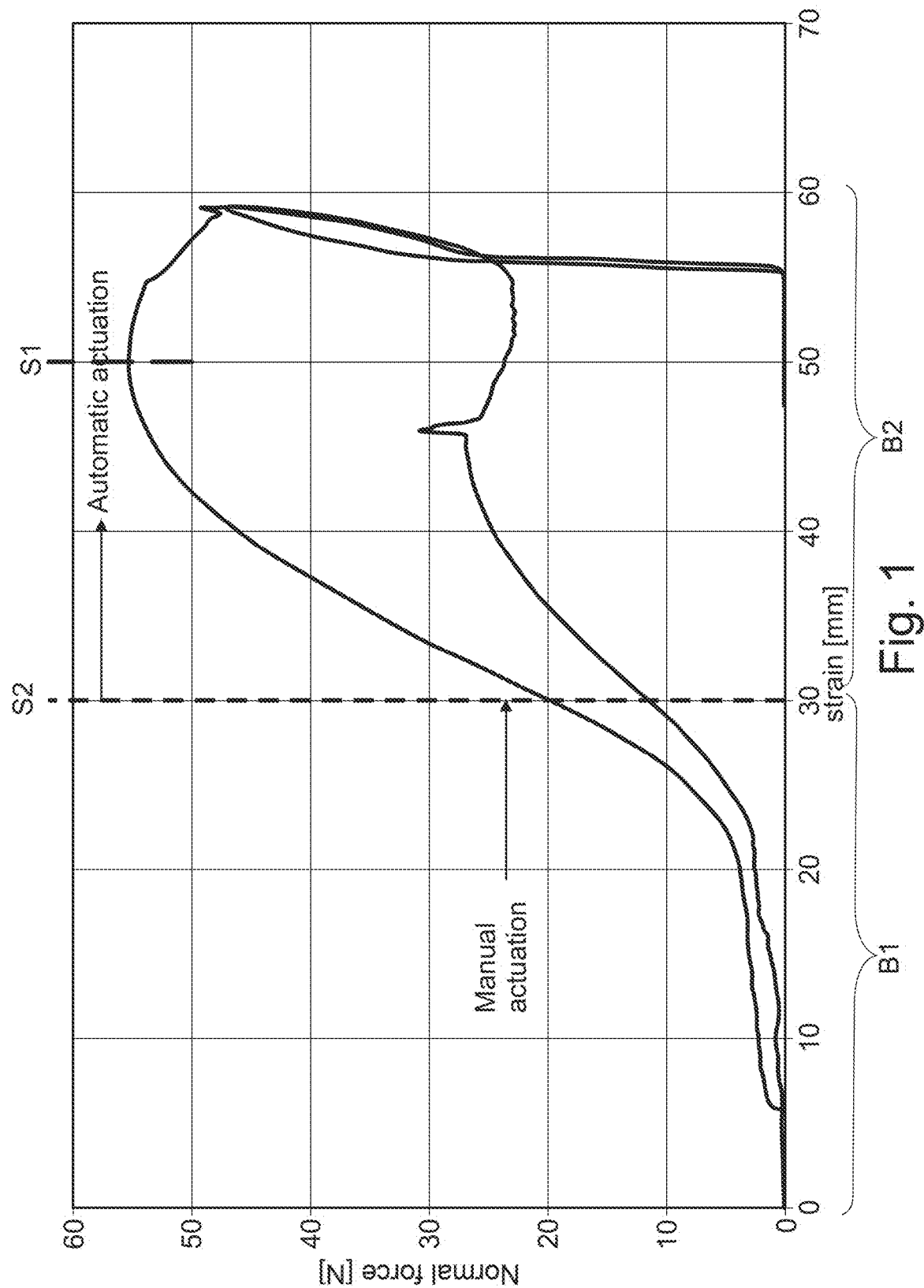
FIG. 1 shows a diagram illustrating the delineation of different working force ranges in relation to an actuation stroke according to a first embodiment of the invention.

FIG. 1 shows a diagram depicting a working force curve or actuating force curve in a combined sealing-cutting instrument 1 in relation to an actuating stroke of a handle element or actuating lever 2 recorded based on a strain gauge according to a first embodiment of the invention. Here, the horizontal axis indicates a strain of the strain gauge [mm] representing the actuation stroke, and the vertical axis indicates an actuation force [N]. It should be noted that the diagram serves to illustrate the delineation of a low-load working force range B1 and a high-load working force range B2, which are traversed within an instrument actuation that has, correspondingly, a preparation phase for preparing patient tissue and a clamping phase for a sealing-cutting process. Proportions and sizes depicted therein are merely exemplary in nature.

It should be noted that while the "sealing-cutting process" may in principle be a simultaneous sealing and cutting of the tissue, e.g., by an appropriately designed electrode, in this preferred embodiment the sealing is performed by electrodes and, as a separate step therefrom, the cutting is performed by a mechanical cutting blade (not shown) which is manually operated by a separate mechanism. The instrument 1 itself is a combined sealing-cutting instrument, which can perform both process parts or steps, in particular within a single clamping phase.

The instrument actuation starts in the diagram at the bottom left in a resting position, where the strain (the actuation stroke), and the actuation force/working force are both "0". Then the preparation phase begins, with a low actuation stroke and a low working force. This corresponds to a manual actuation of a first actuating mechanism 3 having the actuation lever 2 in the low-load working force range B1.

If a user wants to perform tissue sealing, he increases the actuation stroke of the actuation lever 2 until a threshold actuation force is reached, which is hereinafter referred to as a second threshold actuation force S2 according to the above description. In this example, the attainment of the second threshold actuation force S2 is detected by means of the strain gauge as a detection device and thus derived from the actuating stroke of the actuating lever 2 (indirect detection). This corresponds to a transition position of the actuating lever 2, in which an electric motor 4 of a second actuating mechanism 5 is automatically switched on. In this transition position, an automatic change from the low-load working force range B1 to a high-load working force range B2 is carried out, in which the further actuation of the instrument 1 is at least motor-assisted or, in particular, fully automatic. As an alternative to the example described above, the attainment of the second threshold actuation force S2 can be detected, for example, by position or force sensors integrated in the first actuating mechanism 3 or by means of contact activation. Assisted by the electric motor 4 or fully automatically, the working force/actuating force and the actuating stroke are now increased until a maximum clamping force is reached, which corresponds to a first threshold actuation force S1 as described above. The first threshold actuation force S1 can, for example, be detected by the same detection device as the second threshold actuation force S2 or detected and limited based on a preset maximum engine speed. When the first threshold actuation force S1 is reached, the sealing-cutting process can be performed.

Afterwards, the instrument 1 is released from the high-load working posture/position by motor, initiated by a manual initial actuation (in particular in case of a mechanical latching of one of the actuating mechanisms 3, 5 in the high-load working posture/position) or manually, and is manually spring-supported or motor-assisted or fully automatically returned from the high-load working force range B2 back to the low-load working force range B1.

Figure 2:
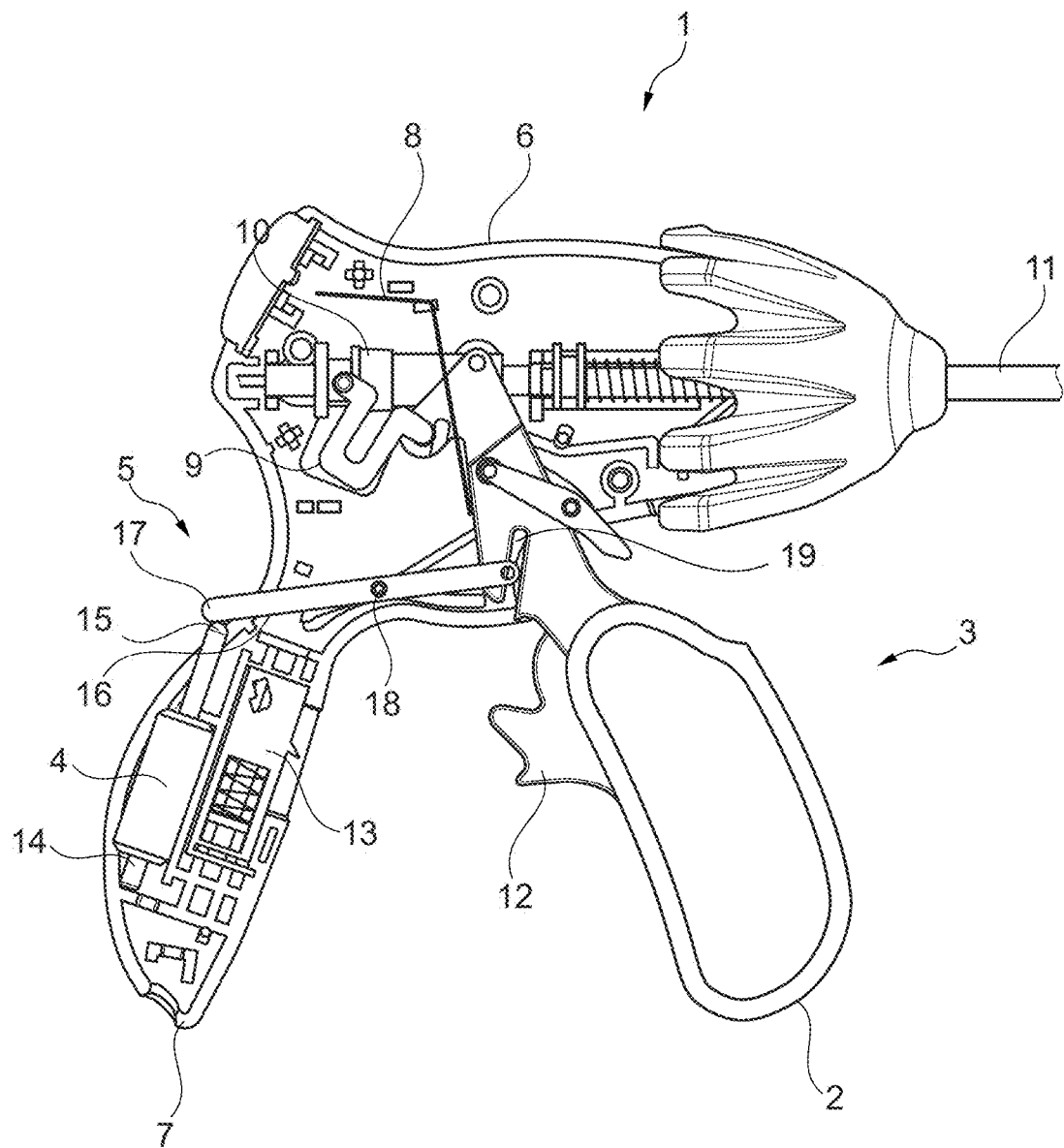
FIG. 2 shows the first embodiment of a combined sealing and cutting instrument according to the invention in a resting position.

FIG. 2 shows a cross-sectional view of the first embodiment of the instrument 1 according to the invention in a resting position, wherein a corresponding sectional plane corresponds to a symmetry plane of the instrument 1. The instrument 1 according to the invention has a pistol-like structure with an instrument housing 6, which has a holding portion 7. Further, the actuating lever 2 is pivotally mounted on the instrument housing 6 at a first, inner end about a bearing axis such that a user with one hand can grasp the holding portion 7 and an exposed second end of the actuating lever 2 and press them together, i.e. pivot them relative to each other, to actuate the instrument 1. A return spring 8 is mounted in the instrument housing 6 and presses against the actuating lever 2 to hold it in the resting position or return it to the resting position.

At the first end of the actuating lever 2, at a distance from the bearing axis, a leg of a U-shaped arc spring 9 is articulated, which is articulated with its second leg to a pulling element 10 and via which the pivoting movement of the actuating lever 2 is converted into an axial movement of the pulling element 10. The pulling element 10 is mounted for axial movement on the instrument shaft 11, which emerges at the mouth of the pistol-like instrument housing 6, and is used to actuate a tool (not shown) with mutually movable instrument branches and electrodes for sealing and a mechanical cutting blade for cutting the patient tissue. The actuating lever 2, the arc spring 9 and the pulling element 10 are part of the first actuating mechanism 3. The arc spring 9 is compressed in the event of an excessive load on the first actuating mechanism 3 and thus serves as an overload protection, in particular in the case of an actuation in the low-load working force range B1, if, for example, the instrument branches already block at a small actuating stroke.

Furthermore, optionally, the actuating lever 2 and the arc spring 9 form a toggle lever for actuating the pulling element 10 to optimize a working force-actuating stroke ratio, i.e., to initially allow a small working force for a large actuating stroke of the pulling element 10 for an actuation and to gradually shift a ratio thereof so that a large working force is achieved for a small actuating stroke of the pulling element 10 in a final range, particularly in the high-load working force range B2.

Figure 3:
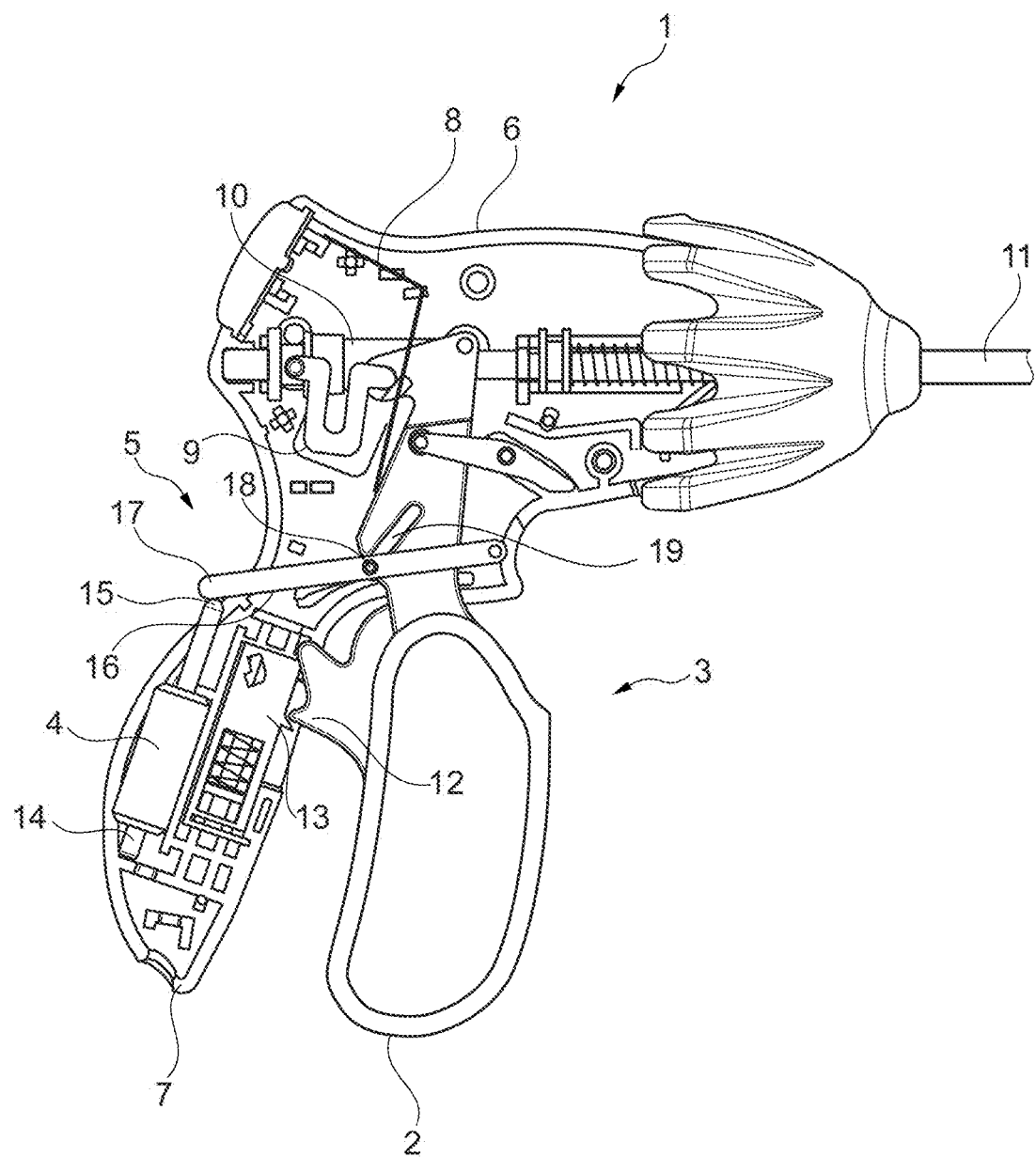
FIG. 3 shows the instrument according to the first embodiment in a transition position.

FIG. 3 shows the instrument 1 according to the invention in a transition position, i.e., at a point in time at which a second threshold actuation force S2 or an actuating stroke associated with this second threshold actuation force S2 has been reached. The first actuating mechanism 3, in particular the actuating lever 2, is provided with a latching lug 12 which, in the transition position, engages in the holding portion 7 and there pushes aside an associated, spring-mounted latching pin 13. The latching pin 13 and the latching lug 12 form a latching mechanism. Furthermore, the attainment of the second threshold actuation force S2 or the corresponding actuating stroke is detected and the electric motor 4, which is arranged in the holding portion 7, is then automatically switched on. For example, for detecting the second threshold actuation force S2, the latching mechanism or a contact between the first and second actuating mechanisms may serve as a switch, strain gauges may be provided on the arc spring 9 for directly measuring the working force, or the like. According to this embodiment example, the electric motor 4 is a linear motor or a rotary motor having a transmission gear for converting a rotary motion generated thereby into a linear motion.

The electric motor 4 has a drive rod 14 which is mounted in the electric motor 4 so as to be axially movable, extending substantially parallel to or slightly inclined with respect to the holding portion 7 of the instrument housing 6. The drive rod 14 is advanced by the electric motor 4. At its one end facing a main part of the instrument housing 6, the drive rod 14 is rounded and forms a tappet 15, which may be formed as a contact for contact activation of the electric motor 4. The tappet 15 abuts a guide surface 16 on a first end of a follower 17 and is adapted to press against the guide surface 16 of the follower 17 when actuated by the electric motor 4. At a second end, the follower 17 is pivotally mounted in the instrument housing 6 about a bearing axis such that a longitudinal axis of the follower 17 intersects a longitudinal axis of the actuating lever 2. Preferably, the follower 17 is fork-shaped or O-shaped and has two arms extending on both sides of the actuating lever 2. A guide pin 18 is arranged in a central section of the follower 17 in such a way that it engages in a guide groove 19 of the actuating lever 2 when the transition position is reached, in order to couple the second actuating mechanism 5 mechanically to the first actuating mechanism 3, i.e. to transmit force. The guide pin 18 may also be arranged in the guide groove 19 before this point, in which case the guide groove 19 is shaped to allow free movement of the actuating lever 2, i.e. without the guide groove 19 transmitting force to the guide pin 18, to ensure complete decoupling of the two actuating mechanisms in the low-load working force range B1. The electric motor 4, the drive rod 14 and the follower 17 are part of the second actuating mechanism 5.

Figure 4:
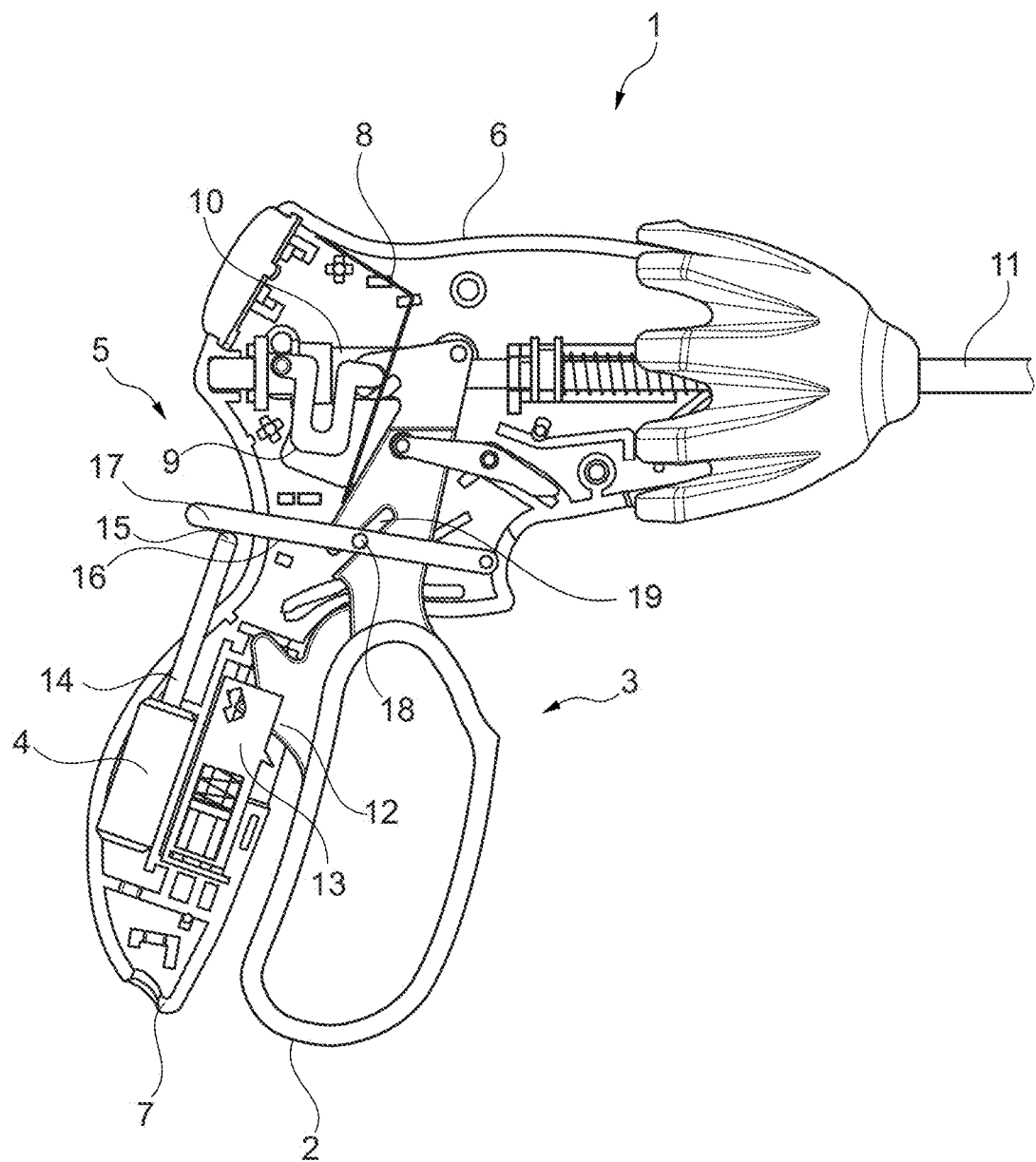
FIG. 4 shows the instrument according to the first embodiment in a working position.

When the electric motor 4 is driven to actuate the instrument 1 in the high-load working force range B2, the drive rod 14 is linearly actuated, pressing with its tappet 15 against the guide surface 16 of the follower 17. This causes the follower 17 to pivot about its bearing axis relative to the instrument housing 6, with the tappet 15 sliding along the guide surface 16 and the guide pin 18 pressing against the guide groove 19 of the actuating lever 2, thus moving it further. The follower 17 serves as a transmission element that allows the power provided by the electric motor 4 to be transmitted with great force to the tool via the first actuating mechanism 3, in order to move the instrument 1 to the high-load working posture/position as shown in FIG. 4. When the high-load working posture/position is reached, the spring-loaded latching pin 13 snaps into the latching lug 12, causing the actuating lever 2 and thus the first actuating mechanism 3, which is mechanically coupled to the second actuating mechanism 5, to engage with the instrument housing 6. To avoid overloading the actuating mechanisms or the tool, the electric motor 4 can only be switched on until a first threshold actuation force S1 or an actuating stroke from which this first threshold actuation force S1 can be derived is reached. Reaching the first threshold actuation force can be detected by the detection device as described above. For example, this a change in position of the first and/or second actuating mechanism 3, 5 can be detected by an incremental encoder or a contact distance (for example between the tappet 15 and the guide surface 16 of the follower 17), or the first threshold actuation force S1 can be determined or adjusted by a limitation of the motor speed. As soon as the high-load working position, which in this embodiment is also the latching position, is reached, the electric motor 4 can be deactivated and, if necessary, the drive rod 14 can be retracted.

In this way, the second actuating mechanism 5, in particular the electric motor 4, is decoupled from the first actuating mechanism 3 when the high-load working posture/position is reached. Moreover, since the first actuating mechanism 3 is also moved during motorized actuation in the high-load working force range B2 (clamping phase), in which the two actuating mechanisms 3, 5 are mechanically coupled, both a release from the high-load working posture/position and the complete return to the resting position can be controlled manually by the user.

Alternatively, it is possible to leave the drive rod 14 extended in the high-load working posture/position with the electric motor 4 switched off in order to switch it on again, if necessary, after an initial manual actuation, e.g. by briefly tapping the actuating lever 2, and to provide motorized assistance for resetting the two actuating mechanisms 3, 5. In this case, the motorized assistance is provided in particular in the actuation area in which the actuation lever 2 is disengaged or released again, since the actuation force for disengaging or releasing the actuation lever 2 is at least as great as that for engaging. Consequently, it makes sense to assist the user not only in engaging but also in disengaging. It should be noted here that a threshold actuation force (pressure point) for disengagement, at which the motorized assistance is switched on, must not be too small in order to prevent the actuation lever 2 from being disengaged unintentionally. In this case, the sealing process would have to be stopped and a corresponding error message would have to be output to the generator. Accordingly, the function is also provided and ensured that the sealing process can be deliberately stopped by disengaging the actuating lever 2. If necessary, the motorized assistance can only be switched on when a force sensor measures the actuation force in the unlatching direction and a certain threshold actuation force is exceeded. In terms of design, the motorized assistance can be implemented in that the drive rod 14 is also coupled to the follower 17 in a pulling direction, for example by a combination of a groove and a pin. Alternatively, the drive rod 14 can come into contact or engagement with the latching pin 13 or a projection arranged thereon at an actuation stroke corresponding to the position of the actuation lever 2 immediately before disengagement, in particular through the second end of the drive rod 14 facing away from the follower 17 or a lug or recessed area formed on the drive rod 14 specifically for this purpose. The latter option makes it possible to provide the motorized assistance exclusively for disengaging the actuating lever and otherwise to allow undisturbed manual guidance.

Figure 5:
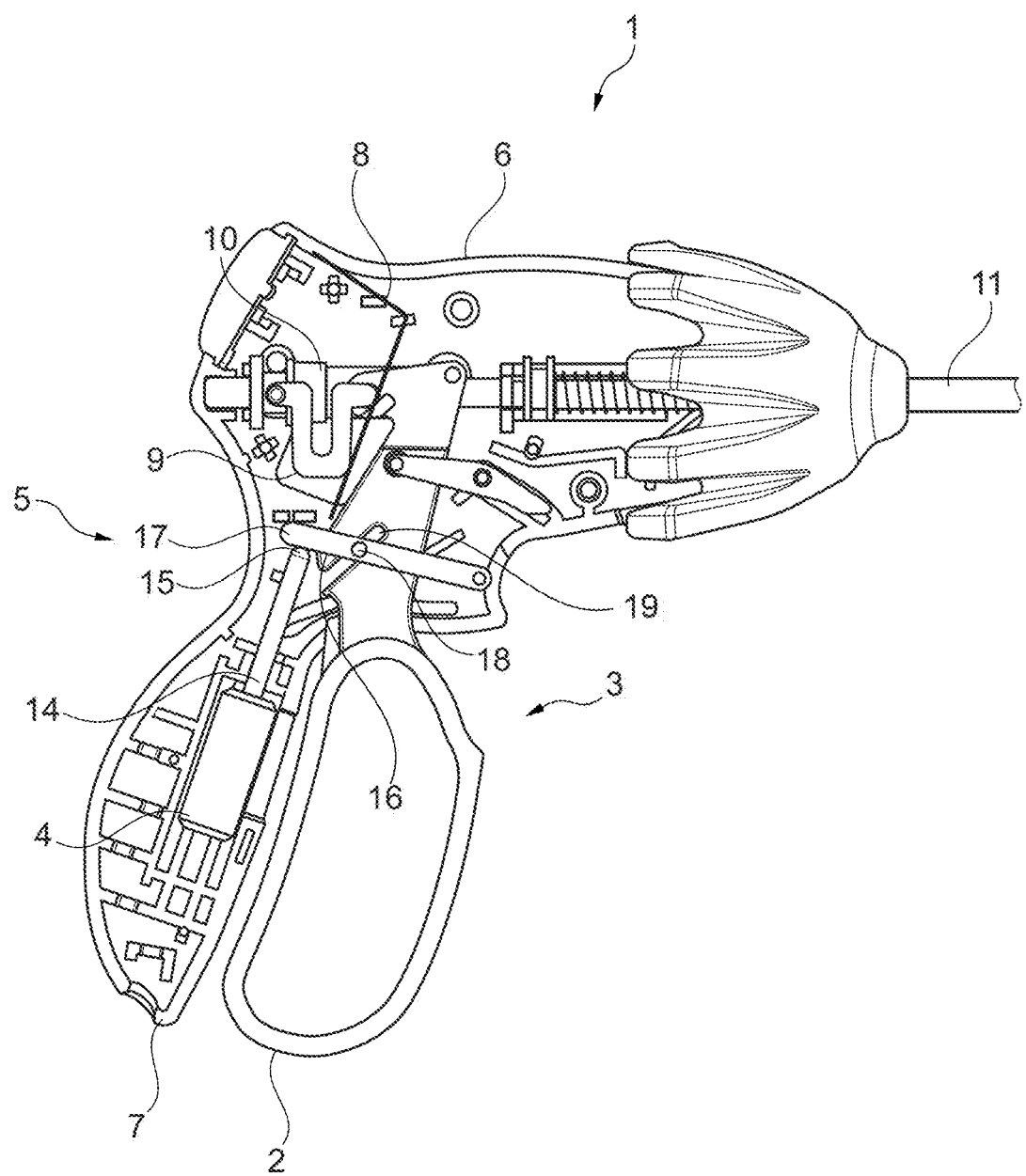
FIG. 5 shows a modified version of the instrument according to the first embodiment in a transition position.

FIG. 5 shows a modified version of the instrument 1 according to the invention according to the first embodiment. This corresponds essentially to the variant described above, which is why only their differences are explained below.

According to this modification, no mechanical latching mechanism, i.e. no latching lug 12 and no spring-loaded latching pin 13, is provided. This makes it possible to reduce the required installation space. Instead, the electric motor 4 remains activated even when the high-load working posture/position is reached and serves as an electrical latching means or holding means to hold the instrument in the high-load working posture/position (clamping position) during the sealing-cutting process. This makes it possible, in particular, to control a clamping duration and a reset of the instrument in the high-load working force range B2 in a fully automatic, precise and, in particular, process-dependent manner. Alternatively, also according to this modification, the reset of the instrument 1 can be manually triggered and or at least partially manually performed.

Figure 6:
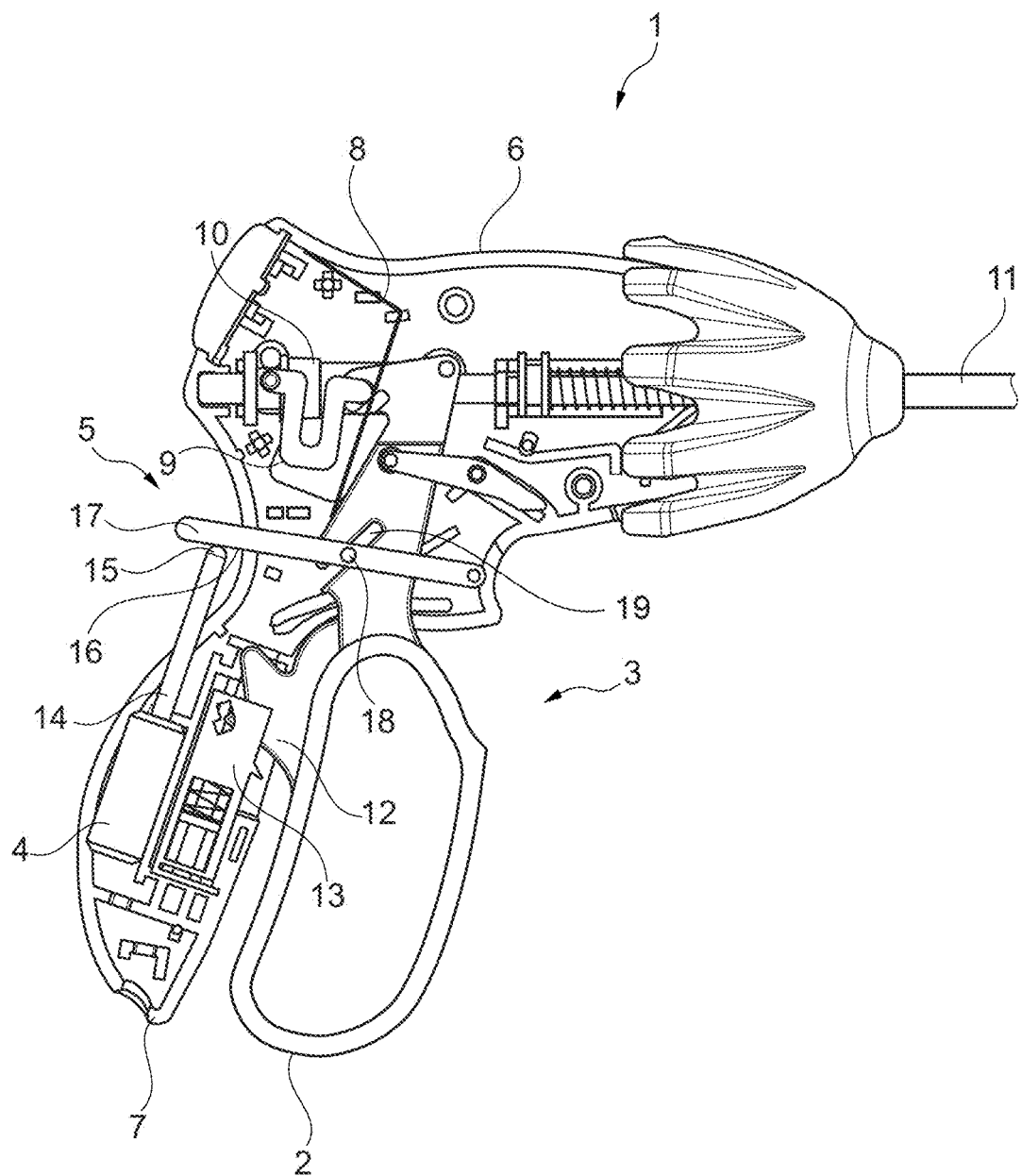
FIG. 6 shows a second embodiment of the combined sealing and cutting instrument according to the invention in a transition position.

FIG. 6 shows a cross-sectional view of the instrument 1 according to the invention according to a second embodiment in a transition position. The mechanical structure of this embodiment corresponds essentially to the first embodiment (unmodified basic variant), which is why reference is made to the above description in this respect. In contrast to the first embodiment, the latching lug 12 and the latching pin 13 that is spring-mounted in the holding portion 7 of the instrument housing 6 are arranged in such a way that they already latch when the high-load working force range B2 is reached, i.e. in the transition position shown, and thus the user receives tactile and/or audible feedback of a termination of the manual actuation phase (preparation phase). Furthermore, for example, the latching mechanism can additionally be used as a switch (e.g. a button or contact) which is actuated when latching takes place, whereby a successful latching serves as a start condition to allow the second actuating mechanism 5 to be switched on or the electric motor 4 to be activated.

That is, the entire actuation stroke of the actuation lever 2 from the resting position to the latching position, which in this embodiment also corresponds to the transition position, is performed manually in the low-load working force range B1, whereby the user can prepare the patient tissue, position the instrument 1 and then bring it into the latching position or into the transition position. When the latching position is reached, the start condition is confirmed, with, for example, the latching mechanism itself serving as a switch or contact confirming the start condition to allow activation of the electric motor 4. If the sealing-cutting process for sealing and cutting the patient tissue is subsequently started, for example by actuating the tool or the electrodes attached thereto by means of a power switch (e.g., high-frequency button), the electric motor 4 is automatically switched on to start tissue clamping in a coordinated manner together with the sealing-cutting process. If the start condition is not met (i.e., if the actuating lever 2 is not latched) and if the energizing switch is nevertheless actuated, the electric motor 4 is not energized and simple tissue clamping-free coagulation is performed, which cannot be performed in terms of the sealing-cutting process (vessel sealing method).

According to this second embodiment, the electric motor 4 serves as an additional latching means by which the second actuating mechanism 5 is held in the high-load working posture/position during the sealing-cutting process. When a preset process duration has elapsed or the sealing-cutting process has been manually aborted, the electric motor 4 automatically moves to the resting position, with the return of the actuating mechanisms 3, 5 in the high-load working force range being fully automatic. When the transition position is reached, the actuating lever 2 must be manually released from the latching position.

In other words, the actuation of the second actuating mechanism 5 in the high-load working force range B2 is directly associated with the sealing-cutting process and is fully automatic and process-controlled (depending on parameters of the sealing-cutting process). Consequently, the present embodiment is characterized by a sealing process-linked control, which is additionally linked to reaching the latching position of the actuating lever 2.

All of the above-described embodiments are characterized by the fact that a tissue clamping for a sealing-cutting process, at least assisted by motor, is automatically switched on when certain standard conditions occurring during the process (i.e., a current supply to the electrodes or a manual exertion of a certain working force) are fulfilled, without any additional operations or actuating movements being required on the part of the user.

Figure 7:
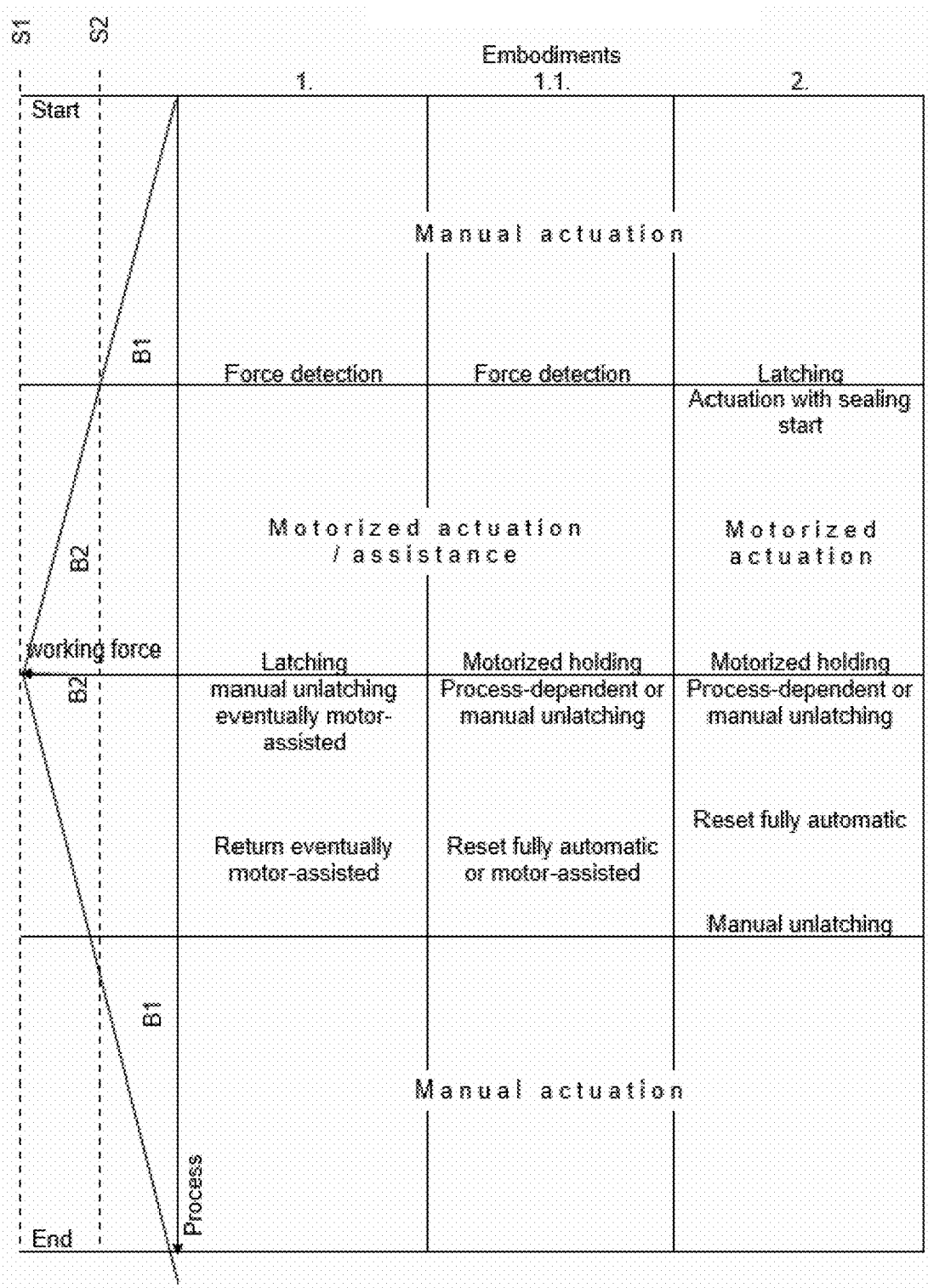
FIG. 7 is an overview in table form of embodiments of the present invention.

FIG. 7 provides an overview in table form of the embodiments of the present invention described above by way of example, with the columns relating to the first embodiment being designated "1.", the modification thereof being designated "1.1", and the second embodiment being designated "2.". On the left of the table, the work force curve is shown in diagrammatic form (diagonally running line). The individual rows each represent an actuation phase, from top to bottom: the preparation phase, the clamping phase, a reset from the high-load working posture/position in the high-load working force range B2, and a reset in the low-load working force range B1. Furthermore, the column separation lines correspondingly represent the rest, transition, or high-load working posture/position.

The invention claimed is:

1. An instrument for use with a bipolar sealing instrument, the instrument having a pistol-like structure with an instrument housing, which has a holding portion comprising:
    a first actuating mechanism configured for a manual clamping actuation of a tool provided at a distal instrument tip, the first actuating mechanism comprising a handle element extending outside the instrument housing adjacent to the holding portion, wherein the handle element is connected to the instrument housing and configured to move relative to the instrument housing sequentially from a resting position, through a low-load working force range, through a high-load working force range, and to a high-load working position, the handle element defining an elongated guide groove having an open end, wherein, in at least in the low-load working force range, the handle element is configured to provide direct, tactile feedback to a user regarding forces on the handle element during movement of the handle element through the low-load working force range; and
    a second actuating mechanism comprising a motor, wherein the second actuating mechanism is configured to enter the open end of the elongated guide groove and advance into the handle element to mechanically couple the second actuating mechanism to the handle element upon movement of the handle element into the high-load working force range, and wherein the motor is configured to be automatically activated upon movement of the handle element into the high-load working force range to thereby move the handle element through the high-load working force range to the high-load working position in a motor-assisted or fully automatic manner, and wherein the motor is configured to hold the handle element in the high-load working force range;
    wherein:
        the handle element is pivotally attached to the instrument housing at a handle element pivot located at a proximal end of the handle element,
        the handle element extends from the handle element pivot to a distal end of the handle element, and
        the elongated guide groove is located between the handle element pivot and the distal end of the handle element.

2. The instrument according to claim 1, wherein the second actuating mechanism is indirectly coupled to the tool via a spring element.

3. The instrument according to claim 1, wherein the second actuating mechanism is configured to return the handle element from the high-load working position to the low-load working force range fully automatically or motor-assisted or manually.

4. The instrument according to claim 1, further comprising a detection device configured to detect a first threshold actuation force or a first threshold actuation position indicating that the high-load working position is reached, wherein upon reaching the first threshold actuation force or the first threshold actuation position:
    the motor is automatically deactivated, or
    the motor is activated to hold the handle element in the high-load working position.

5. The instrument according to claim 4, wherein the detection device is configured to detect a second threshold actuation force or a second threshold actuation position indicating that the handle element has moved into the high-load working force range, wherein the motor of the second actuating mechanism is automatically activated upon reaching the second threshold actuation force or the second threshold actuation position.

6. The instrument according to claim 1, wherein the second actuating mechanism is configured to be held in the high-load working position by the motor.

7. The instrument according to claim 1, wherein the second actuating mechanism is configured to release the handle element from the high-load working position by operation of the motor.

8. The instrument according to claim 1, wherein the handle element is configured to be released from the high-load working position by applying a manual actuation force to initiate release from the high-load working position.

9. The instrument according to claim 1, wherein the instrument is configured to allow a sealing process to be initialized when the motor is activated to hold the handle element in the high-load working position.

10. The instrument according to claim 9, wherein the instrument is configured to allow a sealing process to be initialized while the motor is not activated to hold the handle element in the high-load working position.

11. The instrument according to claim 1, wherein the second actuating mechanism comprises a guide pin that enters the elongated guide groove upon movement of the handle element into the high-load working force range.

12. The instrument according to claim 1, wherein:
the second actuating mechanism comprises guide pin configured to enter the open end of the elongated guide groove when the handle element moves from the low-load working force range to the high-load working force range to mechanically couple the second actuating mechanism; and
the motor is configured to apply a force to the guide pin to drive the guide pin along the elongated guide groove thereby to move the handle element through the high-load working force range to the high-load working position.

13. An instrument for use with a bipolar sealing instrument, the instrument comprising:
a housing comprising a holding portion;
a shaft extending from the housing;
a pulling element movably mounted on the housing and extending into the shaft;
a handle supported on and extending outside the housing to be gripped by a hand, the handle being movable relative to the housing and towards the holding portion through a range of travel sequentially from a resting position, through a low-load working force range, through a high-load working force range, and to a high-load working position;
a pulling element linkage having a pulling element linkage input end connected to the handle at a first location on the handle and a pulling element linkage output end connected to the pulling element, whereby the pulling element linkage is configured to convey a movement of the handle through the range of travel into a corresponding movement of the pulling element relative to the housing;
a motor mounted on the housing; and
a drive linkage having a drive linkage input end operatively connected to the motor and a drive linkage output end, wherein the drive linkage output end is disengaged from the handle when the handle is in the resting position and the low-load working force range, and the drive linkage output end is directly engages the handle at a second location on the handle upon movement of the handle from the low-load working force range to the high-load working force range;
wherein, when the handle is in the high-load working force range, and the high-load working position:
the motor is configured to apply an operating force to the drive linkage input end,
the drive linkage is configured to convey the operating force from the drive linkage input end to the drive linkage output end at the second location on the handle,
the handle is configured to convey the operating force from the second location on the handle to the pulling element linkage input end at the first location on the handle, and
the pulling element linkage is configured to convey the operating force from the pulling element linkage input end at the first location on the handle to the pulling element.

14. The instrument according to claim 13, wherein the pulling element linkage comprises a spring.

15. The instrument according to claim 13, wherein the drive linkage output end and the handle at the second location on the handle comprise a pin that is configured to engage a slot upon movement of the handle from the low-load working force range to the high-load working force range.

16. The instrument according to claim 13, wherein the handle is pivotally connected to the housing at a handle pivot, the first location on the handle is located a first distance from the handle pivot, and the second location on the handle is located at a second distance from the handle pivot and spaced from the first location.

17. The instrument according to claim 16, wherein:
the second location on the handle comprises a first contact surface;
the drive linkage output end comprises a second contact surface; and
the drive linkage is configured to convey the operating force to the handle to move the handle through the high-load working force range and to the high-load working position by sliding contact between the second contact surface and the first contact surface.

18. The instrument according to claim 13, wherein:
the drive linkage comprises a lever pivotally mounted on the housing at a lever pivot;
the drive linkage output end is located on the lever at a location spaced from the lever pivot, and
the motor is configured to apply the operating force to rotate the lever around the lever pivot.

19. The instrument according to claim 13, wherein the motor is configured to hold the handle in the high-load working position.

* * * * *